US012699102B2

(12) United States Patent
Matsumoto et al.

(10) Patent No.: US 12,699,102 B2
(45) Date of Patent: Aug. 4, 2026

(54) COMPOSITION CONTAINING TARC, AND METHOD FOR IMPROVING STORAGE STABILITY OF TARC

(71) Applicant: SEKISUI MEDICAL CO., LTD., Tokyo (JP)

(72) Inventors: Akiko Matsumoto, Tokyo (JP); Tomoyuki Usui, Tokyo (JP); Yuka Suzuki, Tokyo (JP); Kengo Fujimura, Tokyo (JP)

(73) Assignee: SEKISUI MEDICAL CO., LTD., Tokyo (JP)

( * ) Notice: Subject to any disclaimer, the term of this patent is extended or adjusted under 35 U.S.C. 154(b) by 849 days.

(21) Appl. No.: 18/015,210

(22) PCT Filed: Jul. 9, 2021

(86) PCT No.: PCT/JP2021/025903
§ 371 (c)(1),
(2) Date: Jan. 9, 2023

(87) PCT Pub. No.: WO2022/009974
PCT Pub. Date: Jan. 13, 2022

(65) Prior Publication Data
US 2023/0266337 A1      Aug. 24, 2023

(30) Foreign Application Priority Data
Jul. 10, 2020      (JP) ................................. 2020-119025

(51) Int. Cl.
*G01N 33/68*        (2006.01)

(52) U.S. Cl.
CPC ................................ *G01N 33/6863* (2013.01)

(58) Field of Classification Search
CPC ............... G01N 33/6863; G01N 33/96; G01N 2333/521; G01N 2496/25
See application file for complete search history.

(56) References Cited

U.S. PATENT DOCUMENTS 8,669,063 B2 *   3/2014   Weinschenk ............ A61P 35/00
                                                                    435/7.1
2018/0171007 A1 *   6/2018   Boakye ................... A61P 37/08

FOREIGN PATENT DOCUMENTS

| JP | 8-5634 A | 1/1996 |
| JP | 8-12593 A | 1/1996 |
| JP | 2004-125560 A | 4/2004 |
| JP | 2010-230660 A | 10/2010 |
| JP | 2018-130085 A | 8/2018 |
| WO | WO 2015/069865 A1 | 5/2015 |

OTHER PUBLICATIONS

Espacenet English Translation JP2018130085 to Masaru et al. (Year: 2018).*
HISCL TARC Reagent, Oct. 2019, 6. shape structure, 4. precautions for use, SYSMEX Corporation, total 4 pages.
HISCL TARC Reagent, revised Jun. 2021 and Oct. 2019, SYSMEX Corporation, total 9 pages.
International Search Report, issued in PCT/JP2021/025903, PCT/ISA/210, dated Sep. 7, 2021.
Kakinuma et al., "Thymus and activation-regulated chemokine in atopic dermatitis: Serum thymus and activation-regulated chemokine level is closely related with disease activity", J Allergy Clin Immunol, Mar. 2001, vol. 107, No. 3, p. 535-541.
Tamaki et al., "Serum TARC/CCL 17 Levels as a Disease Marker of Atopic Dermatitis", Journal of the Japanese Dermatological Association, 2006, vol. 116, No. 1, p. 27-39.
Written Opinion of the International Searching Authority, issued in PCT/JP2021/025903, PCT/ISA/237, dated Sep. 7, 2021.
Taiwanese Office Action and Search Report for Taiwanese Application No. 110125272, dated Mar. 5, 2025, with English translation of the Office Action.
English translation of International Preliminary Report on Patentability and Written Opinion of the International Searching Authority for International Application No. PCT/JP2021/025903, dated Jan. 10, 2023.
English translation of International Preliminary Report on Patentability for International Application No. PCT/JP2021/025903, dated Jan. 19, 2023.

* cited by examiner

*Primary Examiner* — Kathryn Elizabeth Limbaugh
(74) *Attorney, Agent, or Firm* — Birch, Stewart, Kolasch & Birch, LLP

(57)      ABSTRACT
An object of the present invention is to provide a TARC-containing composition with high storage stability. Provided is a composition including TARC (Thymus and activation-regulated chemokine) and one or more selected from the group consisting of a sugar fatty acid ester-type nonionic surfactant, a polyoxyethylene-polyoxypropylene block copolymer-type nonionic surfactant, and a polyoxyethylene alkylamine-type nonionic surfactant and being in liquid form. The aforementioned object is achieved by the composition.

16 Claims, No Drawings

COMPOSITION CONTAINING TARC, AND METHOD FOR IMPROVING STORAGE STABILITY OF TARC

TECHNICAL FIELD

The present invention relates to a composition containing TARC. More specifically, the present invention relates to a composition capable of stably storing TARC for a long period of time. The present invention also relates to a method and kit for measuring TARC, a method for improving the storage stability of TARC, and a TARC adsorption inhibitor.

BACKGROUND ART

Thymus and activation-regulated chemokine (which may be hereinafter referred to as TARC) is C-C chemokine ligand 17 (CCL17) and is a kind of chemokine having a leukocyte migration activity. TARC attracts Th2 cells, which are one of lymphocytes, to the lesion site to cause IgE production and eosinophil infiltration/activation. It is considered that TARC exacerbates the symptoms of atopic dermatitis by enhancing allergic reactions in this way (Non Patent Literature 1).

Prompt and reliable sedation of atopic dermatitis inflammation is considered important. As compared with other indicators of the disease state of atopic dermatitis such as serum IgE level, peripheral blood eosinophil count, and serum LDH level, TARC matches well with the severity of atopic dermatitis and is considered to reflect the disease state more sensitively (Non Patent Literature 2). Accordingly, use of TARC as a biomarker enables the severity to be grasped objectively and quickly when selecting or changing therapeutic agents for atopic dermatitis, to determine the effects.

A calibration sample needs to be used to quantify a component to be measured in a biological sample. The calibration sample is a sample containing the component to be measured, which is used for applications such as an internal standard or a concentration calibration standard (calibrator). In order to obtain an accurate quantitative value, the calibration sample is required to be stable over time and temperature. The calibration sample is preferably in the form of a fluid solution (which may be hereinafter referred to as "liquid") for ease of operation. In this case, examples of the matter desired for the calibration sample include maintenance of biological activity (such as antigenicity to specific antibodies, binding activity to specific binding partners of antibodies and lectins, physiological activity of peptide hormones, enzyme activity, and three-dimensional structure as a protein for supporting each activity), prevention of adsorption to containers, and maintenance of antiseptic ability.

As a method for storing a calibration sample in liquid form intended for use in an immunoassay, a method of stabilizing an antigen in coexistence with casein and/or whey protein in a calibration sample (Patent Literature 1), a method of stabilizing insulin in coexistence with a bile acid amide derivative (Patent Literature 2), and a method of stabilizing a soluble interleukin-2 receptor (sIL-2R) in coexistence with a chelating agent (Patent Literature 3) are known. Although it is necessary to study the stabilization method according to the properties of the substance to be stabilized, no detailed studies have been conducted on liquid calibration samples for TARC, at present.

CITATION LIST

Patent Literature

Patent Literature 1
Japanese Patent Laid-Open No. 08-005634
Patent Literature 2
Japanese Patent Laid-Open No. 06-012593
Patent Literature 3
Japanese Patent Laid-Open No. 2010-230660

Non Patent Literature

Non Patent Literature 1
J Allergy Clin Immunol 107: 535-541, 2001
Non Patent Literature 2
Journal of the Japanese Dermatological Association 116 (1): 27-39, 2006

SUMMARY OF INVENTION

Technical Problem

It is an object of the present invention to provide a TARC-containing composition with high storage stability.

Solution to Problem

The present inventors attempted to produce a TARC-containing composition with high storage stability. Then, they have found that the stability of TARC is improved when TARC is added to a solution containing one or more selected from the group consisting of a sugar fatty acid ester-type nonionic surfactant, a polyoxyethylene-polyoxypropylene block copolymer-type nonionic surfactant, and a polyoxyethylene alkylamine-type nonionic surfactant. The present invention is based on such findings.

Specifically, the present invention is as follows,
<1> A composition including TARC (Thymus and activation-regulated chemokine) and one or more selected from the group consisting of a sugar fatty acid ester-type nonionic surfactant, a polyoxyethylene-polyoxypropylene block copolymer-type nonionic surfactant, and a polyoxyethylene alkylamine-type nonionic surfactant and being in liquid form.
<2> The composition according to <1>, being a calibration sample solution for measuring TARC.
<3> The composition according to <1> or <2>, being filled in a storage container.
<4> The composition according to <3>, wherein the storage container is plastic.
<5> The composition according to any one of <1> to <4>, wherein the TARC concentration is 10 pg/mL to 1 μg/mL with respect to the composition.
<6> The composition according to any one of <1> to <5>, wherein the concentration of the one or more selected from the group consisting of the sugar fatty acid ester-type nonionic surfactant, the polyoxyethylene-polyoxypropylene block copolymer-type nonionic surfactant, and the polyoxyethylene alkylamine-type nonionic surfactant is 0.00001 mass % to 1 mass % with respect to the composition.
<7> The composition according to any one of <1> to <6>, wherein the sugar fatty acid ester-type nonionic surfactant is a polyoxyethylene sorbitan fatty acid ester-type nonionic surfactant.

<8> The composition according to any one of <1> to <7>, wherein when the TARC concentration is 500 pg/mL with respect to the composition, the TARC residual rate after storage at 37° C. for 28 days in a plastic container is 80% or more.

<9> The composition according to any one of <1> to <8>, wherein when the TARC concentration is 500 pg/mL with respect to the composition, the TARC residual rate after storage at 4° C. for 28 days in a plastic container is 90% or more.

<10> The composition according to any one of <1> to <9>, wherein the sugar fatty acid ester-type nonionic surfactant, the polyoxyethylene-polyoxypropylene block copolymer-type nonionic surfactant, and the polyoxyethylene alkylamine-type nonionic surfactant are polyoxyethylene (20) sorbitan monolaurate, polyoxyethylene (20) sorbitan monooleate, polyoxyethylene-polyoxypropylene condensate, polyoxyethylene (20) cured tallow amine, polyethylene glycol monolaurate, polyoxyethylene lauryl ether, polyethylene glycol mono-p-isooctylphenyl ether, and n-nonanoyl-N-methyl-D-glucamine.

<11> A method for measuring TARC, using the composition according to any one of <1> to <10>.

<12> A kit for measuring TARC, including the composition according to any one of <1> to <10>.

<13> A method for improving the storage stability of TARC, including a step of contacting TARC with a solution containing one or more selected from the group consisting of a sugar fatty acid ester-type nonionic surfactant, a polyoxyethylene-polyoxypropylene block copolymer-type nonionic surfactant, and a polyoxyethylene alkylamine-type nonionic surfactant.

<14> The method for improving the storage stability of TARC according to <13>, wherein the TARC concentration is adjusted so as to be 10 pg/mL to 1 μg/mL with respect to the solution.

<15> The method for improving the storage stability of TARC according to <13> or <14>, wherein the concentration of the one or more selected from the group consisting of a sugar fatty acid ester-type nonionic surfactant, a polyoxyethylene-polyoxypropylene block copolymer-type nonionic surfactant, and a polyoxyethylene alkylamine-type nonionic surfactant in the solution is 0.00001 mass % to 1 mass % with respect to the solution.

<16> The method for improving the storage stability of TARC according to any one of <13> to <15>, wherein the sugar fatty acid ester-type nonionic surfactant is a polyoxyethylene sorbitan fatty acid ester-type nonionic surfactant.

<17> The method for improving the storage stability of TARC according to any one of <13> to <16>, wherein the sugar fatty acid ester-type nonionic surfactant, the polyoxyethylene-polyoxypropylene block copolymer-type nonionic surfactant, and the polyoxyethylene alkylamine-type nonionic surfactant are polyoxyethylene (20) sorbitan monolaurate, polyoxyethylene (20) sorbitan monooleate, polyoxyethylene-polyoxypropylene condensate, polyoxyethylene (20) cured tallow amine, polyethylene glycol monolaurate, polyoxyethylene lauryl ether, polyethylene glycol mono-p-isooctylphenyl ether, and n-nonanoyl-N-methyl-D-glucamine.

<18> An adsorption inhibitor for preventing adsorption of TARC in a solution containing TARC onto a container, including one or more selected from the group consisting of a sugar fatty acid ester-type nonionic surfactant, a polyoxyethylene-polyoxypropylene block copolymer-type nonionic surfactant, and a polyoxyethylene alkylamine-type nonionic surfactant, as an active component.

<19> The adsorption inhibitor according to <18>, wherein the TARC concentration in the solution containing TARC is 10 pg/mL to 1 μg/mL with respect to the solution.

<20> The adsorption inhibitor according to <18> or <19>, to be used so that the surfactant concentration is 0.00001 mass % to 1 mass % with respect to the solution.

<21> The adsorption inhibitor according to any one of <18> to <20>, wherein the sugar fatty acid ester-type nonionic surfactant is a polyoxyethylene sorbitan fatty acid ester-type nonionic surfactant.

<22> The adsorption inhibitor according to any one of <18> to <21>, wherein the sugar fatty acid ester-type nonionic surfactant, the polyoxyethylene-polyoxypropylene block copolymer-type nonionic surfactant, and the polyoxyethylene alkylamine-type nonionic surfactant are polyoxyethylene (20) sorbitan monolaurate, polyoxyethylene (20) sorbitan monooleate, polyoxyethylene-polyoxypropylene condensate, polyoxyethylene (20) cured tallow amine, polyethylene glycol monolaurate, polyoxyethylene lauryl ether, polyethylene glycol mono-p-isooctylphenyl ether, and n-nonanoyl-N-methyl-D-glucamine.

Advantageous Effects of Invention

The present invention can provide a TARC-containing composition with high storage stability, particularly, a TARC-containing calibration sample. Accordingly, the present invention enables TARC in a biological sample to be accurately quantified and the severity of atopic dermatitis to be accurately grasped.

DESCRIPTION OF EMBODIMENTS

TARC

In this description, "TARC" means Thymus and activation-regulated chemokine (CCL17). TARC is a kind of chemokine having leukocyte migration activity. TARC has a function of attracting Th2 cells, which are one of lymphocytes, to the lesion site to produce IgE or infiltrate/activate eosinophils. Use of TARC as a biomarker enables the severity to be grasped objectively and quickly when selecting or changing therapeutic agents for atopic dermatitis.

TARC can be measured by a known method such as immunological technique. Examples of the immunological technique include ELISA, enzyme immunoassay, surface plasmon resonance, latex agglutination immunoassay (LTIA), chemiluminescence immunoassay, electrochemiluminescence immunoassay, fluorescent antibody method, radioimmunoassay, Western blotting, immunochromatography, and high-performance liquid chromatography (HPLC).

The TARC to be contained in the composition of the present invention may be a commercially available product or one produced or purified by oneself. The TARC to be contained in the composition of the present invention may be produced in vitro or extracted from the living body.

Concentration of TARC

The concentration of the TARC to be contained in the composition of the present invention is not limited to the following examples but is preferably 10 pg/mL to 1 µg/mL, more preferably 50 pg/mL to 500 ng/mL, further preferably 100 pg/mL to 100 ng/mL, and most preferably 100 pg/mL to 50 ng/mL, with respect to the composition, in consideration of the stability of TARC.

Surfactant

In this description, a surfactant having a hydrophilic group that does not ionize when dissolved in water is referred to as a nonionic surfactant.

Sugar Fatty Acid Ester-Type Nonionic Surfactant

The sugar fatty acid ester-type nonionic surfactant is a nonionic surfactant having a sugar as a hydrophilic portion and a long-chain fatty acid as a hydrophobic portion and is also referred to as a polyhydric alcohol type. Examples of the sugar fatty acid ester-type nonionic surfactant include a sucrose fatty acid ester-type nonionic surfactant, a sorbitan fatty acid ester-type nonionic surfactant, and a polyoxyethylene sorbitan fatty acid ester-type nonionic surfactant. The sucrose fatty acid ester-type nonionic surfactant is a nonionic surfactant having sucrose as a hydrophilic portion and a long-chain fatty acid as a hydrophobic portion. The sorbitan fatty acid ester-type nonionic surfactant is a nonionic surfactant containing a sorbitan, fatty acid ester that is a partial ester of sorbitol or sorbitan and a long-chain fatty acid.

The number of carbon atoms in the long-chain fatty acid as a hydrophobic portion is not limited, as long as the effects of the present invention are obtained, but is, for example, 12 to 30, preferably 12 to 24, more preferably 12 to 20, and further preferably 12 to 18.

Examples of the sucrose fatty acid ester-type nonionic surfactant that can be used in the composition of the present invention include sucrose stearic acid ester [CAS number: 25168-73-4], sucrose lauric acid ester [CAS number: 25339-99-5], sucrose paimitic acid ester [CAS number: 26446-38-8], and sucrose stearic acid diester [CAS number: 27195-16-0]. Examples of the sorbitan fatty acid ester-type nonionic surfactant that can be used in the composition of the present invention include sorbitan lauric acid monoester [CAS number: 1338-39-2], sorbitan stearic acid monoester [CAS number: 1338-41-6], sorbitan oleic acid monoester [CAS number: 1338-43-8], and sorbitan palmitic acid monoester [CAS number: 26266-57-9].

The composition of the present invention preferably contains a polyoxyethylene sorbitan fatty acid ester-type nonionic surfactant as the sugar fatty acid ester-type nonionic surfactant. The polyoxyethylene sorbitan fatty acid ester-type nonionic surfactant is a nonionic surfactant in which ethylene oxide is added to a sorbitan fatty acid ester that is a partial ester of sorbitol or sorbitan and a long-chain fatty acid.

Among them, at least one selected from the group consisting of polyoxyethylene (20) sorbitan monolaurate, polyoxyethylene (20) sorbitan monostearate, polyoxyethylene (20) sorbitan tristearate, and polyoxyethylene (20) sorbitan monooleate is preferably used, at least one selected from the group consisting of polyoxyethylene (20) sorbitan monolaurate and polyoxyethylene (20) sorbitan tristearate is more preferably used, and polyoxyethylene (20) sorbitan monolaurate is most preferably used.

The details of the four polyoxyethylene sorbitan fatty acid ester-type nonionic surfactants are shown below.

Polyoxyethylene (20) sorbitan monolaurate (Tween 20) [CAS number: 9005-64-5]
Polyoxyethylene (20) sorbitan monostearate (Tween 60) [CAS number: 9005-67-8]
Polyoxyethylene (20) sorbitan tristearate (Tween 65) [CAS number: 9005-71-4]
Polyoxyethylene (20) sorbitan monooleate (Tween 80) [CAS number: 9005-6-6]
Tween is a registered trademark.

Polyoxyethylene-polyoxypropylene Block Copolymer-Type Nonionic Surfactant

The polyoxyethylene-polyoxypropylene block copolymer-type nonionic surfactant is a nonionic surfactant in which ethylene oxide is added using polypropylene glycol as a hydrophobic group and is represented by formula (I).

$$HO(C_2H_4O)a—(C_3H_6O)b—(C_2H_4O)cH \quad [Formula (I)]$$

Herein, a, b, and c represent a degree of polymerization.

The molecular weight of the propylene glycol ($C_3H_6O$) chain that is a hydrophobic group is not limited, as long as the effects of the present invention are obtained, but is, for example, 200 to 10000, preferably 500 to 5000, more preferably 800 to 4000, and further preferably 900 to 4000. Further, the mass % of the ethylene oxide added with respect to the entire molecule is not limited, as long as the effects of the present invention are obtained, but is, for example, 1 to 95%, preferably 5 to 90%, more preferably 5 to 80%, and further preferably 10 to 80%.

Examples of the polyoxyethylene-polyoxyethylene block copolymer-type nonionic surfactant that can be used in the composition of the present invention include Pluronic® Series sold by BASF SE, ADEKA® Pluronic® Series sold by ADEKA CORPORATION, and NEWPOL® PE Series sold by Sanyo Chemical Industries, Ltd. Examples of ADEKA® Pluronic® Series can include L-31 (here, the total value of the degree of polymerization a and the degree of polymerization c (which will be hereinafter referred to as the decree of polymerization a+c) is 3, and the degree of polymerization b is 17), L-44 (here, the degree of polymerization a+c is 20, and the degree of polymerization b is 20), L-61 (here, the degree of polymerization a+c is 5, and the degree of polymerization b is 30), L-64 (here, the degree of polymerization a+c is 25, and the degree of polymerization b is 30), L-121, P-65, P-85 (here, the degree of polymerization a+c is 50, and the degree of polymerization b is 40), P-105, 9-68 (here, the degree of polymerization a+c is 150, and the degree of polymerization b is 30), F-88 (here, the degree of polymerization a+c is 200, and the decree of polymerization b is 40), and 9-108 (here, the degree of polymerization a+c is 300, and the degree of polymerization b is 55). These CAS numbers are all [900-11-6]. Among them, at least one selected from the group consisting of Pluronic® F-68, F-88, and F-108 is preferably used, and Pluronic® F-68 is more preferably used.

Polyoxyethylene alkylamine-Type Nonionic Surfactant

The polyoxyethylene alkylamine-type nonionic surfactant is an amine-type nonionic surfactant that has a polyoxyethylene chain as a hydrophilic portion and a long-chain fatty acid as a hydrophobic portion. The number of carbon atoms in the long-chain fatty acid as a hydrophobic portion is not limited, as long as the effects of the present invention are obtained, but is, for example, 12 to 30, preferably 12 to 24, more preferably 12 to 20, and further preferably 12 to 18. The length of the polyoxyethylene chain as a hydrophilic portion is not limited, as long as the effects of the present invention are obtained, and is, for example, 5 to 50, preferably 5 to 40, and further preferably 7 to 30.

Examples of the polyoxyethylene alkylamine-type nonionic surfactant that can be used in the composition of the present invention can specifically include polyoxyethylene lauryl amine (product name: BLAUNON® L-205, L-207, L-210, and L-230, available from AOKI OIL INDUSTRIAL Co., Ltd.), polyoxyethylene stearyl amine (product name: BLAUNON® S-210, S-215, S-220, and S-230, available from AOKI OIL INDUSTRIAL Co., Ltd.), polyoxyethylene coconut alkylamine [CAS number: 61791-14-8, product name: AMIET® 105, available from Kao Corporation], polyoxyethylene (20) cured tallow amine [CAS number: 61790-82-7, product name: AMIET® 320, available from Kao Corporation], and polyoxyethylene tallow amine (product name: BLAUNON® S-205T, S-220T, S230T, and S-240T, available from AOKI OIL INDUSTRIAL Co., Ltd.). Among them, polyoxyethylene (20) cured tallow amine (Product name: AMIET® 320, available from Kao Corporation) is preferably used.

In the composition of the present invention, the order of addition of the sugar fatty acid ester-type nonionic surfactant, the polyoxyethylene-polyozypropylene block copolymer-type nonionic surfactant, or the polyoxyethylene alkylamine-type nonionic surfactant and the TARC is not specifically limited, as long as the effects of the present invention are obtained.

Concentration of Sugar Fatty Acid Ester-Type, polyoxyethylene-polyoxypropylene Block Copolymer-Type, or polyoxyethylene alkylamine-Type Nonionic Surfactant In the composition of the present invention, the concentration of the sugar fatty acid ester-type, polyoxyethylene-polyoxypropylene block copolymer-type, or polyoxyethylene alkylamine-type nonionic surfactant is not limited to the following examples, but is preferably 0.00001 mass % to 1 mass %, more preferably 0.0001 mass % to 1 mass %, further preferably 0.001 mass % to 0.5 mass %, and most preferably 0.001 mass % to 0.1 mass %, with respect to the composition, in consideration of the stability of TARC.

As long as the effects of the present invention are not impaired, the composition of the present invention may or may not contain a nonionic surfactant other than the sugar fatty acid ester-type, polyoxyethylene-polyoxypropylene block copolymer-type, or polyoxyethylene alkylamine-type nonionic surfactant.

As long as the effects of the present invention are not impaired, the composition of the present invention may or may not contain a surfactant other than nonionic surfactants, such as a cationic surfactant, an anionic surfactant, or an amphoteric surfactant.

Storage Container

The composition of the present invention is preferably filled in a storage container. The material of the storage container is not specifically limited, as long as the effects of the present invention can be obtained, and sealing can be achieved, but at least part or all of the contact area with the composition is plastic [such as an olefinic resin, a styrenic resin, an acrylic resin, a polyester resin, a polycarbonate resin, a fluorine resin, a chlorinated resin (such as polyvinyl chloride), a polyamide resin, a polyacetal resin, a polyphenylene ether resin (such as modified polyphenylene ether), polyarylate, polysulfone, a polyimide resin, a cellulose resin (such as cellulose acetate), and a hydrocarbon resin (including a halogen-substituted product)], a metal (such as aluminum), glass, or the like. Among them, in view of production, transportation, and storage of a calibration sample, plastic or glass is preferable, an olefin resin is preferable among plastics, and polypropylene is more preferable.

The storage container may be made of a single material or two or more materials but is preferably made of a single material. The storage container can include a container body and a cap. In this case, the container body and the cap may be made of different materials. In addition, the storage container, particularly the body part, preferably has transparency to the extent that the liquid content can be seen from the outside.

The form of the storage container may be either hard type or soft type, and examples thereof include ampoules, vials, soft bags, syringe-type containers, and glass bottles. The storage container is preferably in the form of a plastic eyedropper bottle, particularly in the form of a cylindrical eyedropper bottle, including a container body and a cap, for the ease of use and the stability of TARC.

Composition

The composition of the present invention can be used as a calibration sample solution in the measurement of TARC. In this description, the calibration sample solution means a sample solution that is used for accurately measuring a substance to be measured and contains the substance to be measured at a certain concentration. Examples thereof include a standard substance, a calibrator, a control, and an internal standard substance. Examples of supply forms of the composition of the present invention include a solution state prepared in advance by mixing of a solvent with TARC and a sugar fatty acid ester-type nonionic surfactant, a polyoxyethylene-polyoxypropylene block copolymer-type nonionic surfactant, or a polyoxyethylene alkylamine-type nonionic surfactant.

In the TARC measurement method, "using a composition" means using a composition to measure TARC accurately. For example, it means using a liquid composition containing TARC as a calibration sample solution (such as a standard substance, a calibrator, a control, and an internal standard substance).

The pH of the composition of the present invention is, for example, 4.0 to 9.5, 5.0 to 9.0, 6.0 to 8.5, 6.5 to 8.0, or 7.0 to 8.0.

The pH can be adjusted by using a pH adjusting reagent well known to those skilled in the art, such as sodium hydroxide or hydrochloric acid.

The composition of the present invention may have any composition that is not particularly limited as long as it does not impair the effects of the present invention. When TARC is measured by immunoassay, the composition is suitable as long as it does not impair the effects of the present invention, and does not prevent all or part of the reactions constituting the assay system such as antigen-antibody reaction, labeling reaction for detection with biotin-avidin, and enzymatic reaction. Various components generally used in the immunoassay can be appropriately selected and used according to the purpose, including various buffers such as acetic acid, citric acid, phosphoric acid, PBS (phosphate buffered saline), HEPES, MES, Tris, glycine, boric acid, carbonic acid, and Good's buffers, components that promote antigen-antibody reactions (e.g., polymers such as polyethylene glycol and polyvinylpyrrolidone), glycoproteins and peptides (e.g., BSA and casein), amino acids, salts (e.g., sodium chloride and potassium chloride), saccharides (e.g., sucrose and cyclodextrin), and preservatives (e.g., sodium azide and ProClin300). PBS with a pH of 6.5 to 8.0 is preferably used.

In this description, "improvement in storage stability" or "improving the storage stability" means that most of TARC in a solution containing TARC is maintained without decomposing for a long period of time, without changing its structure, or without being adsorbed to a container, so that there is no significant difference between the initial value and the measured value after storage of the TARC in the solution.

More specifically, "improvement in storage stability" or "improving the storage stability" can mean, for example, that 80% or more of TARC in a solution containing TARC at a concentration of 10 pg/mL to 1 µg/mL is maintained without decomposing at 37° C. for 28 days, without changing its structure, or without being adsorbed to a container, so that the measured value of TARC in the solution after storage in a plastic container at 37° C. for 28 days is 80% or more of the initial value.

Further, "improvement in storage stability" or "improving the storage stability" can mean, for example, that 90% or more of TARC in a solution containing TARC at a concentration of 10 pg/mL to 1 µg/mL is maintained without decomposing at 4° C. for 28 days, without changing its structure, or without being adsorbed to a container, so that the measured value of TARC in the solution after storage in a plastic container at 4° C. for 28 days is 90% or more of the initial value.

Biological Sample for Measurement of TARC

The biological sample for TARC measurement is not particularly limited as long as TARC can be measured, but blood, serum, or blood plasma is preferably used. The biological sample may be appropriately pretreated, as required. The biological sample is preferably a biological sample collected from a human.

Kit for Measuring TARC

In the Kit for measuring TARC of the present invention, TARC can be measured conveniently and accurately by using the composition of the present invention. Examples of the Kit for measuring TARC can include a kit using an immunological technique. The Kit for measuring TARC of the present invention can contain a reagent for measuring the TARC concentration in a human body by an immunological technique. Examples of the immunological technique include ELISA, enzyme immunoassay, surface plasmon resonance, latex agglutination immunoassay (LTIA), chemiluminescence immunoassay, electrochemiluminescence immunoassay, fluorescence antibody method, radioimmunoassay, Western blotting, immunocromatography, and high-performance liquid chromatography (HPLC).

The Kit for measuring TARC of the present invention can be used for selecting a treatment method or drug for atopic dermatitis, and for grasping the severity of atopic dermatitis when determining the effects of treatment.

The Kit for measuring TARC of the present invention can also include instructions for use and the like. The Kit for measuring TARC may contain optional components such as a buffer, a stabilizer, a sample diluent, a pH adjuster, and a reaction container.

Method for Improving Storage Stability of TARC

The method for improving the storage stability of TARC of the present invention includes a step of contacting TARC with a solution containing a sugar fatty acid ester-type, polyoxyethylene-polyoxypropylene block copolymer-type, or polyoxyethylene alkylamine-type nonionic surfactant. After the sugar fatty acid ester-type, polyoxyethylene-polyoxypropylene block copolymer-type, or polyoxyethylene alkylamine-type nonionic surfactant is added to the solution, TARC may be added thereto, or after TARC is added to the solution, the sugar fatty acid ester-type, polyoxyethylene-polyoxypropylene block copolymer-type, or polyoxyethylene alkylamine-type nonionic surfactant may be added thereto. The solution is preferably a buffer such as PBS, HEPES, MES, CHES, and Tris. PBS with a pH of 6.5 to 8.0 is more preferably used.

Concentration of TARC

In the method for improving the storage stability of TARC of the present invention, the concentration of TARC contained in the solution is not limited to the following examples, but is preferably 10 pg/mL to 1 µg/mL, more preferably 50 pg/mL to 500 ng/mL, further preferably 100 pg/mL to 100 ng/mL, and most preferably 100 pg/mL to 50 ng/mL, in consideration of the stability of TARC.

Sugar Fatty Acid Ester-Type Nonionic Surfactant

Examples of the sugar fatty acid ester-type nonionic surfactant that can be used in the method for improving the storage stability of TARC of the present invention include a sucrose fatty acid ester-type nonionic surfactant, a sorbitan fatty acid ester-type nonionic surfactant, and a polyoxyethylene sorbitan fatty acid ester-type nonionic surfactant.

The number of carbon atoms in the long-chain fatty acid as a hydrophobic portion is not limited, as long as the effects of the present invention are obtained, and is, for example, 12 to 30, preferably 12 to 24, more preferably 12 to 20, and further preferably 12 to 18.

Examples of the sucrose fatty acid ester-type nonionic surfactant that can be used in the method for improving the storage stability of TARC of the present invention include sucrose stearic acid ester [CAS number: 25168-73-4], sucrose lauric acid ester [CAS number: 25339-99-5], sucrose palmitic acid ester [CAS number: 26446-38-8], and sucrose stearic acid diester [CAS number: 27195-16-0]. Examples of the sorbitan fatty acid ester-type nonionic surfactant that can be used in the method for improving the storage stability of TARC of the present invention include sorbitan lauric acid monoester [CAS number: 1338-39-2], sorbitan stearic acid monoester [CAS number: 1338-41-6], sorbitan oleic acid monoester [CAS number: 1338-43-8], and sorbitan palmitic acid monoester [CAS number: 26266-57-9].

In the method for improving the storage stability of TARC of the present invention, a polyoxyethylene sorbitan fatty acid ester-type nonionic surfactant is preferably used as the sugar fatty acid ester-type nonionic surfactant.

Among them, at least one selected from the group consisting of polyoxyethylene (20) sorbitan monolaurate, polyoxyethylene (20) sorbitan monostearate, polyoxyethylene (20) sorbitan tristearate, and polyoxyethylene (20) sorbitan monooleate is preferably used, at least one selected from the group consisting of polyoxyethylene (20) sorbitan monolaurate and polyoxyethylene (20) sorbitan tristearate is more preferably used, and polyoxyethylene (20) sorbitan mono-laurate is most preferably used.

Polyoxyethylene-polyoxypropylene Block Copolymer-Type Nonionic Surfactant

The polyoxyethylene-polyoxypropylene block copoly-mer-type nonionic surfactant is a nonionic surfactant in which ethylene oxide is added using polypropylene glycol as a hydrophobic group and is represented by formula (I).

$$HO(C_2H_4O)a—(C_3H_6O)b—(C_2H_4O)cH \quad [Formula \ (I)]$$

Herein, a, b, and c represent a degree of polymerization.

The molecular weight of the propylene glycol ($C_3H_6O$) chain that is a hydrophobic group is not limited, as long as the effects of the present invention are obtained, but is, for example, 200 to 10000, preferably 500 to 5000, more preferably 800 to 4000, and further preferably 900 to 4000. Further, the mass % of the ethylene oxide added with respect to the entire molecule is not limited, as long as the effects of the present invention are obtained, but is, for example, 1 to 95%, preferably 5 to 90%, more preferably 5 to 80%, and further preferably 10 to 80%.

Examples of the polyoxyethylene-polyoxyethylene block copolymer-type nonionic surfactant that can be used in the composition of the present invention include Pluronic® Series sold by BASF SE, ADEKA® Pluronic® Series sold by ADEKA CORPORATION, and NEWPOL® PE Series sold by Sanyo Chemical Industries, Ltd. Examples of ADEKA® Pluronic® Series can include L-31 (here, the degree of polymerization a+c is 3, and the degree of polym-erization b is 17), L-44 (here, the degree of polymerization a+c is 20, and the degree of polymerization b is 20), L-61 (here, the degree of polymerization a+c is 5, and the degree of polymerization b is 30), L-64 (here, the degree of polym-erization a+c is 25, and the degree of polymerization b is 30), L-121, P-65, P-85 (here, the degree of polymerization a+c is 50, and the degree of polymerization b is 40), P-105, F-68 (here, the degree of polymerization a+c is 150, and the degree of polymerization b is 30), F-88 (here, the degree of polymerization a+c is 200, and the degree of polymerization b is 40), and F-108 (here, the degree of polymerization a+c is 300, and the degree of polymerization b is 55). These CAS numbers are all [9003-11-6]. Among them, at least one selected from the group consisting of Pluronic® F-68, F-88, and F-108 is preferably used, and Pluronic® F-68 is more preferably used.

Polyoxyethylene alkylamine-Type Non-Ionic Surfactant

The polyoxyethylene alkylamine-type nonionic surfactant is an amine-type nonionic surfactant that has a polyoxyeth-ylene chain as a hydrophilic portion and a long-chain fatty acid as a hydrophobic portion. The number of carbon atoms in the long-chain fatty acid as a hydrophobic portion is not limited, as long as the effects of the present invention are obtained, and is, for example, 12 to 30, preferably 12 to 24, more preferably 12 to 20, and further preferably 12 to 18. The length of the polyoxyethylene chain as a hydrophilic portion is not limited, as long as the effects of the present invention are obtained, but is, for example, 5 to 50, prefer-ably 5 to 40, and further preferably 7 to 30.

Examples of the polyoxyethylene alkylamine-type non-ionic surfactant that can be used in the composition of the present invention can specifically include polyoxyethylene lauryl amine (product name: BLAUNON® L-205, L-207, L-210, and L-230, available from AOKI OIL INDUSTRIAL Co., Ltd.), polyoxyethylene stearyl amine (product name: BLAUNON® S-210, S-215, S-220, and S-230, available from AOKI OIL INDUSTRIAL Co., Ltd.), polyoxyethylene coconut alkylamine [CAS number: 61791-14-8, product name: AMIET® 105, available from Kao Corporation], polyoxyethylene (20) cured tallow amine [CAS number: 61790-82-7, product name: AMIET® 320, available from Kao Corporation], and polyoxyethylene tallow amine (prod-uct name: BLAUNON® S-205T, S-220T, S230T, and S-240T, available from AOKI OIL INDUSTRIAL Co., Ltd.). Among them, polyoxyethylene (20) cured tallow amine (Product name: AMIET® 320, available from Kao Corporation) is preferably used.

In the composition of the present invention, the order of addition of the sugar fatty acid ester-type nonionic surfac-tant, the polyoxyethylene-polyoxypropylene block copoly-mer-type nonionic surfactant, or the polyoxyethylene alkylamine-type nonionic surfactant and the TARC is not particularly limited, as long as the effects of the present invention are obtained.

Concentration of Sugar Fatty Acid Ester-Type, polyoxyethylene-polyoxypropylene Block Copolymer-Type, or polyoxyethylene alkylamine-Type Nonionic Surfactant In the method for improving the storage stability of TARC of the present invention, the concentration of the sugar fatty acid ester-type, polyoxyethylene-polyoxypropylene block copolymer-type, or polyoxyethylene alkylamine-type non-ionic surfactant is not limited to the following examples, but is preferably 0.00001 mass % to 1 mass %, more preferably 0.0001 mass % to 1 mass %, further preferably 0.001 mass % to 0.5 mass, and most preferably 0.001 mass % to 0.1 mass %, in consideration of the stability of TARC, with respect to the solution.

TARC Adsorption Inhibitor

The TARC adsorption inhibitor of the present invention includes a sugar fatty acid ester-type, polyoxyethylene-polyoxypropylene block copolymer-type, or polyoxyethyl-ene alkylamine-type nonionic surfactant. The TARC adsorp-tion inhibitor containing the sugar fatty acid ester-type, polyoxyethylene-polyoxypropylene block copolymer-type, or polyoxyethylene alkylamine-type nonionic surfactant may be added to a storage container before contacting a solution containing TARC, or the sugar fatty, acid ester-type, polyoxyethylene-polyoxypropylene block copolymer-type, or polyoxyethylene alkylamine-type nonionic surfactant added as an adsorption inhibitor to a TARC-containing solution in advance may be added to a storage container.

Then, the present invention will be specifically described by way of Examples, but these do not limit the scope of the present invention. In this description, % refers to mass %, unless otherwise specified. The product names, ingredient names, and distributors of the surfactants used in the examples are as follows.

Tween® 20, ingredient name: polyoxyethylene (20) sor-bitan monolaurate, available from FUJIFILM Wako Pure Chemical Corporation Tween® 80, ingredient name: polyoxyethylene (20) sor-bitan monooleate, available from FUJIFILM Wako Pure Chemical Corporation Pluronic® F-68, ingredient name: polyoxyethylene-polyoxypropylene condensate, available from ADEKA CORPORATION AMIET® 320, ingredient name: polyoxyethylene (20) cured tallow amine, available from Kao Corporation EMANON® 1112, ingredient name: polyethylene glycol monolaurate, available from Kao Corporation Brij® 35, ingredient name: polyoxyethylene lauryl ether, available from KISHIDA CHEMICAL Co., Ltd.

Triton® X-100, ingredient name: polyethylene glycol mono-p-isooctylphenyl ether, available from KISHIDA CHEMICAL Co., Ltd.

MEGA-9, ingredient name: n-nonanoyl-N-methyl-D-glucamine, available from DOJINDO LABORATORIES

EXAMPLES

Example 1: Study on Type of Nonionic Surfactant

The storage stability of TARC when stored in plastic eyedropper bottles was tested. The test method and the evaluation method are as follows. A solution having the following constituents was used as a storage solution.

PBS (PH 7.2)

1 mass % BSA

Surfactant (concentration, product name, and type are described in Tables 1 and 4)

(1) Storage Condition 0.5 ml of a TARC liquid storage solution at each concentration was dispensed into plastic eyedropper bottles and stored at 37° C. for 28 days or at 4° C. for 28 days. The TARC concentration was tested at 500 pg/mL, 2000 pg/mL, and 10000 pg/mL.

(2) Measurement Method

Measurement was performed by latex agglutination immunoassay using two types of antibodies. The constituents of the reagents and the measurement method are shown below. Using first reagent and second reagent, measurement was performed using a HITACHI automatic analyzer.

—First Reagent 100 mM MOPS-NaOH (PH 7.5)

500 mM NaCl 0.5% BSA

—Second Reagent

Anti-human TARC monoclonal antibody sensitized latex (two types)

5 mM MOPS-NaOH (PH 7.0)

Anti-Human TARC monoclonal antibodies were obtained using commercially available TARC antigens by methods well known to those skilled in the art. Examples of the commercially available TARC antigens included CCL17, thymus and activation regulated chemokine (Shenandoah Biotechnology, Inc.), CCL17/TARC, Human (LifeSpan Bioscience, Inc.), and Human TARC (CCL17) (Abeomics, Inc.). Further, a combination of monoclonal antibodies capable of a sandwich assay against the TARC antigen was selected by a method well known to those skilled in the art. The anti-human TARC monoclonal antibody sensitized latex was prepared with reference to the method described in Japanese Patent Laid-Open No. 2017-181377.

First, 120 μL of the first reagent was added to 2.4 μL of the TARC liquid storage solution at each concentration. After heating at 37° C. for 5 minutes, 40 μL of the second reagent was added and stirred. Thereafter, absorbance changes for 5 minutes were measured at a dominant wavelength of 570 nm and a secondary wavelength of 800 nm. The absorbance changes measured were converted to TARC concentrations using a calibration curve obtained by measuring standard substances of known concentrations.

(3) Calculation of TARC Residual Rate (%)

For the TARC concentration of each TARC liquid storage solution after storage at 37° C. for 28 days or at 4° C. for 28 days, the TARC residual rate (%) was calculated using the following formula.

TARC residual rate (%)=TARC concentration of each TARC liquid storage solution after storage at 37° C. for 28 days or at 4° C. for 28 days in an eyedropper bottle (pg/mL)/TARC concentration of TARC liquid storage solution immediately after preparation (pg/mL)×100

(4) Table 1 shows the concentration of the surfactant used under each condition, and Tables 2 and 3 show the evaluation results. The TARC residual rate (%) was calculated based on the average of three experiments.

TABLE 1

Concentration, product name, type of surfactant used in each condition

| | Nonionic surfactant | | |
| --- | --- | --- | --- |
| Condition | Concentration (mass %) | Product name | Type |
| 1 | — | None | None |
| 2 | 0.01% | Tween 20 | Polyoxyethylene sorbitan |
| 3 | 0.01% | Tween 80 | fatty acid ester type |
| 4 | 0.01% | Pluronic F68 | Polyoxyethylene-polyoxypropylene block copolymer type |
| 5 | 0.01% | AMIET 320 | Polyoxyethylene alkylamine type |
| 6 | 0.01% | EMANON 1112 | Polyethylene glycol fatty acid ester type |
| 7 | 0.01% | Brij 35 | Alcohol type |
| 8 | 0.01% | TritonX-100 | Alkylphenol type |
| 9 | 0.01% | MEGA-9 | Sugar amide type |

TABLE 2

Evaluation results (TARC residual rate (%) when stored at 37° C. for 28 days)

| Condition | TARC 500 pg/ml sample | TARC 2000 pg/ml sample | TARC 10000 pg/ml sample |
| --- | --- | --- | --- |
| 1 | 47.2 | 86.4 | 87.3 |
| 2 | 90.5 | 94.0 | 95.2 |
| 3 | 92.8 | 88.7 | 96.5 |
| 4 | 89.3 | 89.7 | 94.1 |
| 5 | 107.0 | 90.7 | 94.1 |
| 6 | 75.8 | 89.9 | 94.4 |
| 7 | 67.7 | 96.0 | 90.8 |
| 8 | 78.8 | 95.2 | 96.1 |
| 9 | 72.7 | 91.4 | 90.5 |

When the TARC concentration was 500 pg/mL, the residual rate after 28 days was 47.2% in condition 1 in which no surfactant was added, which was a significantly low result. In conditions 2 and 3 in which a sugar fatty acid ester-type nonionic surfactant was added, in condition 4 is which a polyoxyethylene-polyoxypropylene block copolymer-type nonionic surfactant was added, and in condition 5 in which a polyoxyethylene alkylamine-type nonionic surfactant was added, the residual rate after 28 days was 89.3 to 107.0%. In any surfactant used in conditions 2 to 5, the residual rate after 28 days was improved. Meanwhile, in conditions 6 to 9 using a nonionic surfactant that is not sugar fatty acid ester-type, polyoxyethylene-polyoxypropylene block copolymer-type, or polyoxyethylene alkylamine-type, the residual rate after 28 days was 67.7 to 78.8%, which was improved as compared with that in condition 1 but was lower than in conditions 2 to 5 in which the surfactant found in the present application was added. Likewise, even when the initial concentration was 2000 pg/mL or 10000 pg/mL, the residual rate after 28 days was improved in conditions 2 to 5 using a sugar fatty acid ester-type, polyoxyethylene-polyoxypropylene block copolymer-type, or polyoxyethylene alkylamine-type nonionic surfactant as compared with that in condition 1. This was considered because adsorption of TARC onto the wall surface of the container could be prevented by addition of the sugar fatty acid ester-type, polyoxyethylene-polyoxypropylene block copolymer-type, or polyoxyethylene alkylamine-type nonionic surfactant, or the structural changes of TARC during storage could be suppressed, in conditions in which the residual rate was improved.

TABLE 3

| | Evaluation results (TARC residual rate (%) when stored at 4° C. for 28 days) | | |
|---|---|---|---|
| Condition | TARC 500 pg/ml sample | TARC 2000 pg/ml sample | TARC 10000 pg/ml sample |
| 1 | 65.7 | 86.6 | 92.6 |
| 2 | 109.3 | 99.4 | 99.6 |
| 3 | 113.4 | 99.6 | 103.1 |
| 4 | 110.3 | 99.3 | 98.0 |
| 5 | 94.1 | 97.8 | 100.8 |

When the TARC concentration was 500 pg/mL, the residual rate after 28 days was 65.7% in condition 1 in which no surfactant was added, which was a significantly low result. In conditions 2 and 3 in which a sugar fatty acid ester-type nonionic surfactant was added, in condition 4 in which a polyoxyethylene-polyoxypropylene block copolymer-type nonionic surfactant was added, and in condition 5 in which a polyoxyethylene alkylamine-type nonionic surfactant was added, the residual rate after 28 days was 94.1 to 113.4%. In any surfactant, the residual rate after 28 days was improved. Likewise, even when the initial concentration was 2000 pg/mL or 10000 pg/mL, the residual rate after 28 days was improved in conditions 2 to 5 in which a sugar fatty acid ester-type, polyoxyethylene-polyoxypropylene block copolymer-type, or polyoxyethylene alkylamine-type nonionic surfactant was added.

It was demonstrated as above that coexistence of a sugar fatty acid ester-type, polyoxyethylene-polyoxypropylene block copolymer-type, or polyoxyethylene alkylamine-type nonionic surfactant and TARC improves the storage stability of TARC when stored in plastic eyedropper bottles. This was considered because adsorption of TARC onto the wall surface of the container could be prevented by addition of the sugar fatty acid ester-type, polyoxyethylene-polyoxypropylene block copolymer-type, or polyoxyethylene alkylamine-type nonionic surfactant, or the structural changes of TARC during storage could be suppressed, in conditions in which the residual rate was improved.

Example 2: Study on Surfactant Concentration

Subsequently, the surfactant concentration having an effect of improving the storage stability of TARC was examined using a sugar fatty acid ester-type nonionic surfactant, Tween20 in the same manner as above. Table 4 shows the surfactant concentration used in each condition, and Table 5 and Table 6 show the evaluation results. The TARC residual rate (%) was calculated based on the average of three experiments.

TABLE 4

| | Concentration, product name, type of surfactant used in each condition | | |
|---|---|---|---|
| | | Surfactant | |
| Condition | Concentration (mass %) | Product name | Type |
| 1 | — | None | None |
| 10 | 0.0016% | Tween 20 | Polyoxyethylene sorbitan fatty acid ester type |
| 11 | 0.008% | | |
| 12 | 0.01% | | |
| 13 | 0.20% | | |

TABLE 5

| | Evaluation results (TARC residual rate (%) when stored at 37° C. for 28 days) | | |
|---|---|---|---|
| Condition | TARC 500 pg/ml sample | TARC 2000 pg/ml sample | TARC 10000 pg/ml sample |
| 1 | 47.2 | 86.4 | 87.3 |
| 10 | 88.1 | 92.8 | 96.7 |
| 11 | 88.7 | 91.4 | 98.0 |
| 12 | 90.5 | 94.0 | 95.2 |
| 13 | 85.1 | 94.3 | 95.2 |

TABLE 6

| | Evaluation results (TARC residual rate (%) when stored at 4° C. for 28 days) | | |
|---|---|---|---|
| Condition | TARC 500 pg/ml sample | TARC 2000 pg/ml sample | TARC 10000 pg/ml sample |
| 1 | 65.7 | 86.6 | 92.6 |
| 10 | 109.5 | 104.6 | 101.8 |
| 11 | 101.4 | 101.6 | 103.2 |
| 12 | 109.3 | 99.4 | 99.6 |
| 13 | 98.0 | 101.1 | 100.7 |

When stored at 37° C. (Table 5) and a TARC concentration of 500 pg/mL, the residual rate after 28 days was 47.2% in condition 1 in which no surfactant was added, which was a significantly low result. In conditions 10 to 13 in which 0.0016 to 0.20% of a sugar fatty acid ester-type nonionic surfactant was added, the residual rate after 28 days was 85.1 to 90.5%, which means the residual rate after 28 days was improved at any surfactant concentration. Likewise, even when the initial concentration was 2000 pg/mL or 10000 pg/mL, the residual rate after 28 days was improved in conditions 10 to 13 in which a sugar fatty acid ester-type nonionic surfactant was added.

When stored at 4° C. (Table 6) and a TARC concentration of 500 pg/mL, the residual rate after 28 days was 65.7% in condition 1 in which no surfactant was added, which was a significantly low result. In conditions 10 to 13 in which 0.0016 to 0.20% of a sugar fatty acid ester-type nonionic surfactant was added, the residual rate after 28 days was 98.0 to 109.5%, which means the residual rate after 28 days was improved at any surfactant concentration. Likewise, even when the initial concentration was 2000 pg/mL or 10000 pg/mL, the residual rate after 28 days was improved in conditions 10 to 13 in which a sugar fatty acid ester-type nonionic surfactant was added.

It was demonstrated as above that addition of 0.0016 to 0.20% of a sugar fatty acid ester-type nonionic surfactant to the TARC composition improved the storage stability of TARC when stored in plastic eyedropper bottles. This was considered because adsorption of TARC onto the wall surface of the container could be prevented by addition of the sugar fatty acid ester-type nonionic surfactant, or the structural changes of TARC during storage could be suppressed.

INDUSTRIAL APPLICABILITY

The present invention can provide a TARC-containing composition with high storage stability, particularly, a TARC-containing calibration sample.

The invention claimed is:

1. A composition comprising:
   TARC (Thymus and activation-regulated chemokine); and
   one or more selected from the group consisting of a sugar fatty acid ester-type nonionic surfactant, a polyoxyethylene-polyoxypropylene block copolymer-type nonionic surfactant, and a polyoxyethylene alkylamine-type nonionic surfactant, and
   being in liquid form,
   wherein the TARC concentration is 100 μg/mL to 50 ng/ml with respect to the composition, and
   wherein the composition is filled in a storage container.

2. The composition according to claim 1, wherein the composition is a calibration sample solution for measuring TARC.

3. The composition according to claim 1, wherein the storage container is plastic.

4. The composition according to claim 1, wherein the concentration of the one or more selected from the group consisting of the sugar fatty acid ester-type nonionic surfactant, the polyoxyethylene-polyoxypropylene block copolymer-type nonionic surfactant, and the polyoxyethylene alkylamine-type nonionic surfactant is 0.00001 mass % to 1 mass % with respect to the composition.

5. The composition according to claim 1, wherein the sugar fatty acid ester-type nonionic surfactant is a polyoxyethylene sorbitan fatty acid ester-type nonionic surfactant.

6. The composition according to claim 1, wherein when the TARC concentration is 500 μg/mL with respect to the composition, the TARC residual rate is 80% or more after storage at 37° C. for 28 days in a plastic container.

7. The composition according to claim 1, wherein when the TARC concentration is 500 μg/mL with respect to the composition, the TARC residual rate is 90% or more after storage at 4° C. for 28 days in a plastic container.

8. The composition according to claim 1, wherein the sugar fatty acid ester-type nonionic surfactant is polyoxyethylene (20) sorbitan monolaurate, or polyoxyethylene (20) sorbitan monooleate; the polyoxyethylene-polyoxypropylene block copolymer-type nonionic surfactant is polyoxyethylene-polyoxypropylene condensate; and the polyoxyethylene alkylamine-type nonionic surfactant is polyoxyethylene (20) cured tallow amine.

9. A kit for measuring TARC, wherein the kit comprises the composition according to claim 1.

10. A method for improving storage stability of TARC, comprising a step of contacting TARC with a solution containing one or more selected from the group consisting of a sugar fatty acid ester-type nonionic surfactant, a polyoxyethylene-polyoxypropylene block copolymer-type nonionic surfactant, and a polyoxyethylene alkylamine-type nonionic surfactant,
   wherein the TARC concentration is adjusted so as to be 100 μg/mL to 50 ng/ml with respect to the solution.

11. The method for improving the storage stability of TARC according to claim 10, wherein a concentration of the one or more selected from the group consisting of a sugar fatty acid ester-type nonionic surfactant, a polyoxyethylene-polyoxypropylene block copolymer-type nonionic surfactant, and a polyoxyethylene alkylamine-type nonionic surfactant in the solution is 0.00001 mass % to 1 mass % with respect to the solution.

12. The method for improving the storage stability of TARC according to claim 10, wherein the sugar fatty acid ester-type nonionic surfactant is a polyoxyethylene sorbitan fatty acid ester-type nonionic surfactant.

13. The method for improving the storage stability of TARC according to claim 10, wherein the sugar fatty acid ester-type nonionic surfactant is polyoxyethylene (20) sorbitan monolaurate, or polyoxyethylene (20) sorbitan monooleate; the polyoxyethylene-polyoxypropylene block copolymer-type nonionic surfactant is polyoxyethylene-polyoxypropylene condensate; and the polyoxyethylene alkylamine-type nonionic surfactant is polyoxyethylene (20) cured tallow amine.

14. A method for preventing adsorption of TARC in a solution containing TARC onto a container, comprising:
   a step of adding a TARC adsorption inhibitor containing one or more selected from the group consisting of a sugar fatty acid ester-type nonionic surfactant, a polyoxyethylene-polyoxypropylene block copolymer-type nonionic surfactant, and a polyoxyethylene alkylamine-type nonionic surfactant, as active component, to the container, and
   a step of adding TARC to the container.

15. The method according to claim 14, wherein the sugar fatty acid ester-type nonionic surfactant is a polyoxyethylene sorbitan fatty acid ester-type nonionic surfactant.

16. The method according to claim 14, wherein the sugar fatty acid ester-type nonionic surfactant is polyoxyethylene (20) sorbitan monolaurate, or polyoxyethylene (20) sorbitan monooleate; the polyoxyethylene-polyoxypropylene block copolymer-type nonionic surfactant is polyoxyethylene-polyoxypropylene condensate; and the polyoxyethylene alkylamine-type nonionic surfactant is polyoxyethylene (20) cured tallow amine.

* * * * *